United States Patent [19]

Froilan

[11] Patent Number: 4,530,354

[45] Date of Patent: Jul. 23, 1985

[54] ENDOTRACHAEL TUBE AND HOLDER

[76] Inventor: Faustino C. Froilan, 101 Crabapple La., Morris, Ill. 60450

[21] Appl. No.: 464,260

[22] Filed: Feb. 7, 1983

[51] Int. Cl.³ .............................................. A61M 25/02
[52] U.S. Cl. ................................................. 128/207.17
[58] Field of Search ...................... 128/200.26, 207.14, 128/207.15, 207.16, 207.17

[56] References Cited

U.S. PATENT DOCUMENTS

| | | | |
|---|---|---|---|
| 2,786,469 | 3/1957 | Cohen | 128/200.26 |
| 4,090,518 | 5/1978 | Elam | 128/207.15 |
| 4,235,229 | 11/1980 | Ranford et al. | 128/207.17 |
| 4,249,529 | 2/1981 | Neston et al. | 128/207.17 |
| 4,270,529 | 6/1981 | Muto | 128/207.17 |

FOREIGN PATENT DOCUMENTS 197807  7/1978  France ............... 128/207.17

OTHER PUBLICATIONS

Bizzari-Giuffrida Endoesophageal Tube, 1959, Darol Catalog.

Primary Examiner—Henry J. Recla
Attorney, Agent, or Firm—Ernest Kettelson

[57] ABSTRACT

An endotracheal tube and holder comprising a flexible elongated endotracheal tube for insertion through a patient's mouth down into the patient's trachea to facilitate opening of the airways and a holder to keep the endotracheal tube in place after it has been appropriately inserted. The holder in accordance with this invention comprises a short sleeve having an inner diameter corresponding to the outer diameter of the endotracheal tube and slightly larger to permit the endotracheal tube to slide within the sleeve but still be held snugly within the sleeve when the tube is secured thereto, the sleeve portion of the holder being integrally connected to a base portion which comprises a relatively thin flat strip of flexible sheet material extending outwardly from each side of the sleeve. The outer end of the endotracheal tube has formed thereon a gear rack and the sleeve of the holder includes a pinion gear mounted for rotation on the sleeve wall with the gear teeth extending into the passageway of the sleeve a sufficient distance to engage the corresponding teeth of the gear rack on the endotracheal tube. A knob is attached to the pinion gear whereby the physician can rotate the pinion gear and move the endotracheal tube outwardly from the patient's trachea a pre-selected distance and back inwardly of the patient's trachea by rotating the pinion gear in the opposite direction.

4 Claims, 7 Drawing Figures

ENDOTRACHAEL TUBE AND HOLDER

BACKGROUND OF THE INVENTION

This invention relates to the field of endotracheal tubes for use by physicians in opening the airways of patients in need of such treatment, and devices to hold such endotracheal tube in the desired position.

Prior art devices to hold the endotracheal tube in position include a frame-like member which is secured in place over a patient's mouth and held by a strap around the back of the patient's head or neck, such frame member including a slot in which the endotracheal tube is placed after which it is tied to the frame and held within this slot formed in the frame member. However, it is difficult if not impossible to hold the endotracheal tube securely by this method and prior art devices so as to prevent the tube from reciprocal movement inwardly and outwardly of the patient's mouth, throat and trachea. In other words, the endotracheal tube is subject to movement inwardly and outwardly of the patient's trachea when, for example, the patient moves his head, attempts to turn over, attempts to arise and other bodily movements. Such inward and outward movement of the endotracheal tube can cause severe discomfort to the patient and under certain circumstances, can also cause irritation and injury to the lining of the throat and trachea of the patient.

Somewhat related prior art devices are tracheostomy tubes, but they require an incision through the patient's neck and insertion of the tracheostomy tube through such incision into the throat and trachea of the patient. Such devices are not typically used if the patient's condition will permit the use of an endotracheal tube through the patient's mouth, and in some cases through the patient's nose, down through the internal passageways to the patient's trachea. The use of a tracheostomy tube requires surgery with its attendant complications such as infection, hemorrhage and the like.

Examples of prior art devices of this kind are disclosed in prior art U.S. Pat. Nos. 4,315,505; 4,304,228; 4,270,529; 4,235,229; 4,223,671; 4,033,353; 3,774,616; 3,693,624; 2,820,457; and 2,693,182.

Endotracheal tubes include an inflatable cuff at the lower end for helping to open the air passageway, to aid in suction of the material from the trachea of the patient through the tracheal tube, and to block the area surrounding the tube so food and fluids cannot pass into the bronchi and lungs. A small flexible air line extends from the inflatable balloon portion alongside the wall of the endotracheal tube and extends out through the mouth of the patient having an adapter or a mouthpiece connected at the outer end of the air line through which the cuff can be inflated. The holder for the endotracheal tube in accordance with this invention includes a sleeve having an inner diameter corresponding to the outer diameter of the endotracheal tube, and is slightly larger to receive the endotracheal tube through the sleeve for sliding movement but small enough to securely hold the tube in place when fastened to the sleeve portion of the holder by adhesive strips or the like.

The endotracheal tube should preferably be moved outwardly periodically for a short distance and then reinserted to its original position. It is not necessary to completely remove the endotracheal tube from the patient each day. In order to facilitate the outward movement of the endotracheal tube and reinsertion to its original position, a rack and pinion assembly is incorporated in the holder and endotracheal tube in accordance with this invention. This enables the physician to move the tube inwardly and outwardly by merely rotating the pinion gear, and he can easily determine precisely how far outwardly the endotracheal tube is being moved and also the precise position to reinsert the endotracheal tube by markings on the wall of the tube adjacent the gear rack formed thereon.

SUMMARY OF THE INVENTION

It is an object of the invention to provide an endotracheal tube and holder wherein the holder is better able to secure the endotracheal tube from inward and outward movement as well as from lateral movement after it has been inserted through a patient's mouth into the patient's trachea.

It is an object of the invention to provide an endotracheal tube and holder wherein the holder includes a sleeve member having an inner diameter corresponding to the outer diameter of the endotracheal tube and being just slightly larger to enable the endotracheal tube to slide within the sleeve but yet can be held securely by the sleeve portion of the holder after the endotracheal tube has been secured thereto by adhesive tape or the like, the sleeve portion of the holder being integrally connected to a flat flexible sheet base portion extending outwardly from opposite sides of the sleeve portion, the base portion having an elastic strap connected to each opposite end for securing the device to the head of a patient when the endotracheal tube is in place.

It is an object of the invention to provide an endotracheal tube and holder wherein the outward portion of the endotracheal tube includes a rack gear formed along one side of its outer wall, and the sleeve portion of the holder includes a pinion gear rotatably mounted thereon with its gear teeth extending through the wall of the sleeve into the passageway of the sleeve for engagement with the teeth of the gear rack on the wall of the endotracheal tube, whereby the endotracheal tube may be moved inwardly and outwardly of a patient's trachea by rotating the pinion gear.

DESCRIPTION OF THE PREFERRED EMBODIMENT

Figure 1:
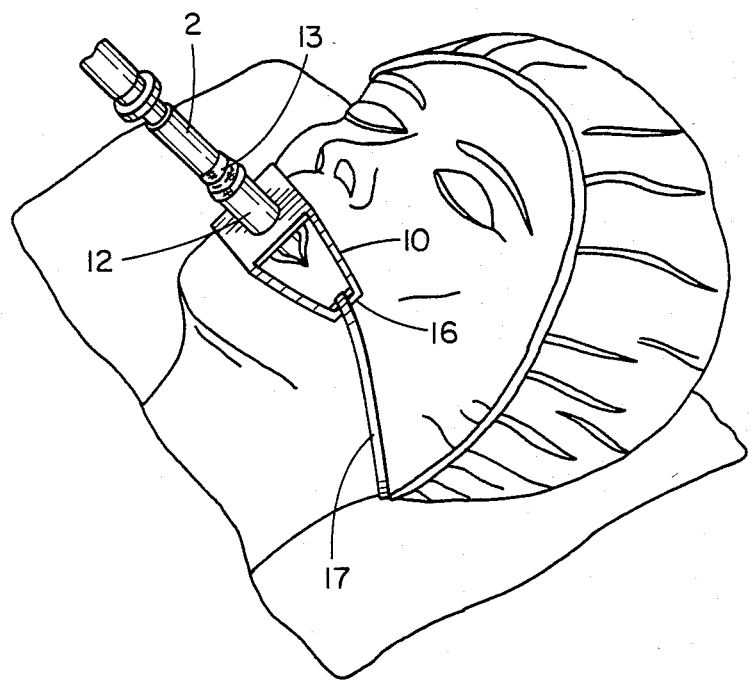
FIG. 1 is a perspective view of a patient having an endotracheal tube held in place by a holder in accordance with this invention.
Figure 2:
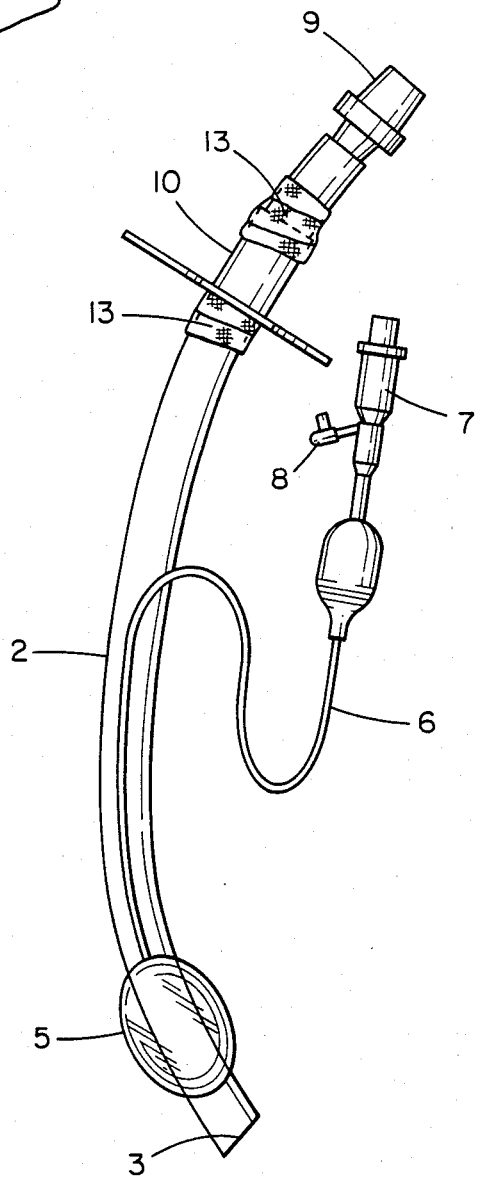
FIG. 2 is an elevation view of an endotracheal tube and holder in accordance with this invention.
Figure 3:
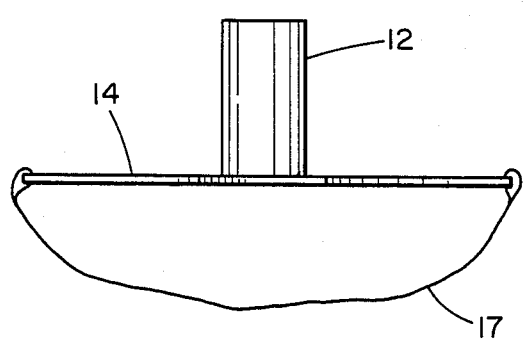
FIG. 3 is an elevation view of the holder in accordance with this invention.
Figure 4:
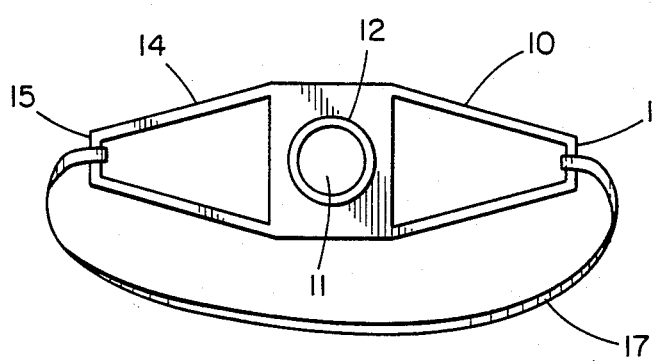
FIG. 4 is a plan veiw of the holder shown in FIG. 3.

This invention includes an endotracheal tube medical device 1 comprising an elongated tubular member 2 having an insertable end 3 and an outer end 4. An inflatable cuff member 5 is formed around the elongated tubular member 2 a short distance inwardly from the insertable end 3. When the elongated tubular member is inserted through a patient's mouth into the patient's trachea, the inflatable cuff member 5 is inflated to form a pneumatic seal around the patient's trachea to prevent escape of air and also to prevent food or liquid from passing into the bronchi and lungs of the patient. A small diameter air line 6 is connected to the inflatable cuff member 5 and is adhered to the outer wall of the elongated tubular member for a sufficient distance to extend outwardly of a patient's mouth when the endotracheal tube 1 is inserted to the proper depth into a patient's trachea. The air line 6 continues and extends freely beyond the point to which it is adhered to the tube wall for a sufficient distance to enable the physician to inflate the cuff member 5. The outer end of the air line 6 is fitted with an adapter 7 through which inflatable cuff member 5 can be inflated. The adapter includes a closure cap 8 to close its outer end after inflation of the cuff member 5 has been completed to prevent air from escaping.

The outer end 4 of the elongated tubular member 2 projects outwardly from a patient's mouth after the endotracheal tube medical device 1 has been properly inserted. The outer end 4 is fitted with a valve or air fitting 9 which may be connected to a respirator to assist the patient in breathing.

Before the valve or air fitting 9 is inserted into the outer end 4 of the tubular member 2, the tube holder 10 in accordance with this invention is put in place by threading the outer end 4 of the tubular member 2 through the passageway 11 of the sleeve portion 12 of the tube holder 10. The sleeve portion 12 of the tube holder 10 is elongated and has an inner diameter which corresponds to the outer diameter of the elongated tubular member 2 and is slightly larger than the outer diameter of the tubular member 2 whereby the tubular member 2 is able to slide inwardly and outwardly of the sleeve portion 12 of the tube holder 10 but in sliding frictional engagement therewith. The inner diameter of the sleeve portion 12 is close enough in dimension to the outer diameter of the tubular member 2 whereby the tubular member 2 is frictionally held snugly and firmly in place within the sleeve portion 12 when the tubular member 2 is secured thereto by fastening means such as adhesive tapes 13. The sleeve portion 12 of the tube holder 10 is integrally connected at one end to the base portion 14 of the tube holder 10 which comprises a relatively flat flexible sheet member which projects outwardly from opposite sides of the sleeve portion 12, the base portion 14 terminating at each opposite end in side edges 15 and 16. An elastic strap 17 is connected to the respective side edges 15 and 16 to extend around the head or neck of a patient when the tube holder 10 is in place with the endotracheal tube 1 extending through the patient's mouth down into the patient's trachea. The sleeve portion 12 of the holder 10 may be of varying length, such as from two centimeters to four centimeters long for a typical endotracheal tube.

Figure 5:
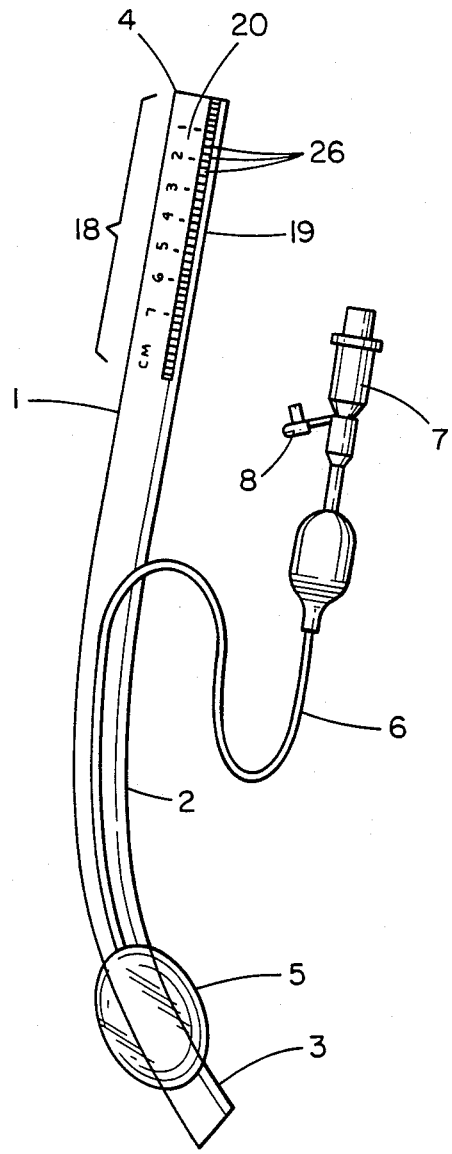
FIG. 5 is an elevation view of a modified endotracheal tube in accordance with this invention having a gear rack formed on the upper portion of its side wall.
Figure 6:
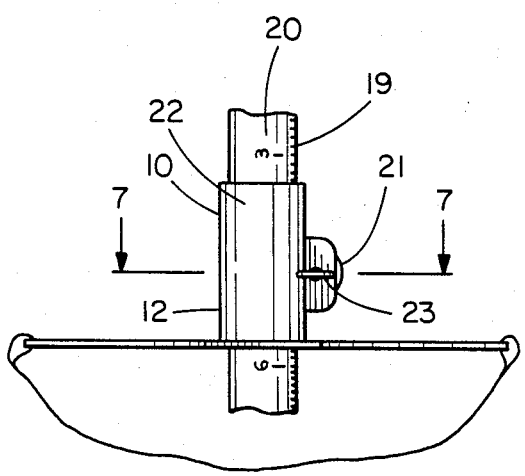
FIG. 6 is an elevation view of a modified holder in accordance with this invention having a pinion gear mounted along the side wall of the sleeve of said holder.
Figure 7:
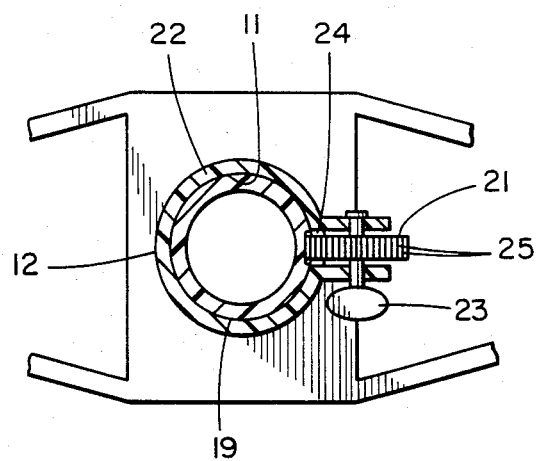
FIG. 7 is a section view taken on line 7—7 of FIG. 6.

In a modification of this invention as shown in FIGS. 5 through 7, the outer region 18 of the elongated tubular member 2 includes a gear rack 19 formed along a portion of one side of the outer wall 20 of the said outer region 18 of the elongated tubular member 2. The gear rack extends longitudinally of the tubular member 2 and teminates at the outer end 4 thereof. The gear rack 19 extends inwardly from the outer end 4 a sufficient distance to reach approximately to the base portion 14 of the tube holder 10 when the endotracheal tube 1 is properly inserted into a patient's trachea and the tube holder 10 is secured in place over the patient's mouth. In this modification, the tube holder 10 includes a pinion gear 21 mounted along the side wall 22 of the sleeve portion 12. A turning knob 23 is connected to the pinion gear as described hereinbelow. The pinion gear 21 extends through an opening 24 in the side wall 22 of the sleeve portion 12 through which the gear teeth 25 of the pinion gear 21 extend to engage the corresponding gear teeth 26 of the gear rack 19 on the outer wall 20 of the outer region 18 of the elongated tubular member 2. Thus, when the endotracheal tube medical device in accordance with this modification of the invention is in place in a patient, the physician can move the elongated tubular member 2 outwardly a pre-selected and desired distance and then reinsert the elongated tubular member 2 back into its original position within the patient's trachea by appropriate rotation of the pinion gear 21. The elongated tubular member 2 has to be periodically, such as on a daily basis, moved from its original completely inserted position within a patient outwardly for a pre-selected distance but without removing the endotracheal tube completely in accordance with good medical practice. A typically desired distance for moving the elongated tubular member 2 outwardly from its original fully inserted position is approximately seven or eight centimeters. Therefore, in a typical endotracheal tube medical device 1 in accordance with this modification of the invention the gear rack 19 may be approximately eight centimerers in length extending inwardly approximately that distance from its outer end 4. The physician may, of course, decide in his judgment that the tubular member 2 need not be moved outwardly a full seven or eight centimeters but can move the elongated tubular member 2 outwardly whatever lesser distance he may desire. The outer wall 20 of the outer region 18 of tubular member 2 has centimeter markings thereon or other appropriate markings whereby the physician can determine precisely the distance the elongated tubular member 2 is moved outwardly when the pinion gear 2 is rotated and he can determine precisely the distance to reinsert the elongated tubular member 2 to place it back in its original position. If it is desired to reinsert the elongated tubular member 2 a slightly different distance so as to position the inflatable end 3 at a slightly different location within the trachea of the patient, the physician can do that too with this modification of this invention.

The elongated tubular member 2 is preferably made of a relatively soft or pliable and flexible material, and a material which has no physical or chemical reactivity, no tissue toxicity, no allergic manifestation and no carcinogenic potential. Some of the materials which are used in making the elongated tubular members of endotracheal tubes include teflon, nylon, polyethylene, polyvinylchloride and silicone. The medical literature regarding endotracheal tubes should be consulted to determine the relative advantages and some disadvantages as well as precautions to observe regarding each of the materials listed.

The rack gear 19 which is formed on the outer wall 20 of the outer region 18 of the tubular member 2 may also be made of a plastic or polymeric material, but one which is sufficiently hard or rigid to form the gear teeth 26 of the rack 19 therein. The rack 19 may be separately bonded to the elongated tubular member 2 by heat sealing or by an appropriate adhesive or cement.

The tube holder 10 and its sleeve 12 may be made of the same material as the elongated tubular member 2.

The base portion 14 of the tube holder 10 includes cutaway portions of the interior thereof to avoid unnecessary obstruction of the patient's mouth when in place to hold the elongated tubular member 2 in its proper inserted position.

I claim:

1. An endotracheal tube and holder comprising an elongated tubular member having a first outer end and a second insertable end to insert into the trachea of a patient, a holding member to hold said elongated tubular member in place when so inserted, said holding member including first elongated retaining means to frictionally engage an elongated peripheral wall portion of said elongated tubular member to hold it against any substantial lateral movement relative to said holding member, and second retaining means to hold said tubular member against any substantial longitudinal movement relative to said holding member, wherein said first elongated retaining means of said holding member comprises a tubular sleeve portion, said elongated tubular member being slidably received in said tubular sleeve portion, wherein said elongated tubular member includes an elongated gear rack positioned on its outer wall, longitudinally thereof, extending from a point inwardly of said first outer end toward said first outer end, and wherein said second retaining means includes a pinion gear rotatably mounted along the outer wall of said tubular sleeve portion of said holding member, an opening in said outer wall to permit gear teeth of said pinion gear to extend through said opening into the tubular passageway of said tubular sleeve portion to engage the gear teeth of said gear rack when said elongated tubular member is inserted through said passageway with its said gear rack positioned to face and engage said gear teeth of said pinion gear, said pinion gear thereby holding said tubular member against any substantial longitudinal movement relative to said holding member until rotated.

2. An endotracheal tube and holder as set forth in claim 1, wherein said pinion gear includes hand grasp means connected thereto for a user to manually grasp and rotate said pinion gear in engagement with said rack of said elongated tubular member, whereby said elongated tubular member may be moved longitudinally in the direction outwardly of a patient's trachea when said pinion gear is rotated in one direction and in the opposite direction inwardly of said patient's trachea when said pinion gear is rotated in the opposite direction.

3. An endotracheal tube and holder as set forth in claim 2, including markings on said elongated tubular member adjacent said gear rack to measure and indicate the distance said elongated tubular member may be moved longitudinally relative to said tubular sleeve portion.

4. An endotracheal tube and holder as set forth in claim 1, wherein said elongated tubular member is made of a relatively soft, flexible polymeric material, said gear rack is made of a relatively hard rigid polymeric material, said rack being bonded to the outer side wall of said elongated tubular member.

* * * * *